(12) United States Patent
Gunther

(10) Patent No.: US 7,332,272 B1
(45) Date of Patent: Feb. 19, 2008

(54) METHOD FOR SCREENING AND IDENTIFYING PHARMACEUTICAL AGENTS

(76) Inventor: Erik Gunther, 34 Bryan Rd., Bradford, CT (US) 06405

( * ) Notice: Subject to any disclaimer, the term of this patent is extended or adjusted under 35 U.S.C. 154(b) by 291 days.

(21) Appl. No.: 09/935,557

(22) Filed: Aug. 22, 2001

Related U.S. Application Data

(60) Provisional application No. 60/254,028, filed on Dec. 6, 2000.

(51) Int. Cl.
  *C12Q 1/68* (2006.01)
  *C12P 21/06* (2006.01)
  *G06F 19/00* (2006.01)
(52) U.S. Cl. .............................. 435/6; 435/69.1; 702/19
(58) Field of Classification Search .................... 435/6, 435/19.1; 702/19
See application file for complete search history.

(56) References Cited

U.S. PATENT DOCUMENTS

| | | | |
|---|---|---|---|
| 5,965,352 A | 10/1999 | Stoughton et al. | |
| 6,110,711 A | 8/2000 | Serafini et al. | |
| 6,165,709 A | 12/2000 | Friend et al. | |
| 6,368,794 B1 * | 4/2002 | Daniel et al. | ................. 435/6 |

FOREIGN PATENT DOCUMENTS

WO 00/15851 A1 3/2000

OTHER PUBLICATIONS

Marton et al. (Nature Medicine (1998) vol. 4, No. 11, pp. 1293-1301.*
Gunther, E.C., et al., "Prediction of clincal drug efficacy by classification of drug-induced genomic expression profiles in vitro," CuraGen Corp., manuscript submitted to *PNAS* May 1, 2003.
Hughes, T.R., et al., "Functional Discovery via a Compendium of Expression Profiles," *Cell 102*:109-126, Jul. 7, 2000.
Peltonen, L. and V.A. McKusick, "Genomics and Medicine: Dissecting Human Disease in the Postgenomic Era," *Science 291*(5507):1224-1228, Feb. 16, 2001.
Gould Rothberg, B.E., et al., "Integrating Expression-Based Drug Response and SNP-Based Pharmacogenetic Strategies Into a Single Comprehensive Pharmacogenomics Program," *Drug Development Research 49*:54-64, 2000.
Gray, N.S., et al., "Exploiting Chemical Libraries, Structure, and Genomics in the Search for Kinase Inhibitors," Science 281:533-538, 1998.
Lockhart, D.J., and E.A. Winzeler, "Genomics, Gene Expression and DNA Arrays," Nature 405:827-836, 2000.
Lueking, A., et al., "Protein Microarrays for Gene Expression and Antibody Screening," Analytical Biochemistry 270:103-111, 1999.
Macbeath, G., and S.L. Schreiber, "Printing Proteins as Microarrays for High-Throughput Function Determination," Science 289:1760-1763, 2000.
Marton, M.J., et al. "Drug Target Validation and Identification of Secondary Drug Target Effects Using DNA Microarrays," Nature Medicine 4(11):1293-1301, 1998.
Ross, D.T., et al., "Systematic Variation in Gene Expression Patterns in Human Cancer Cell Lines," Nature Genetics 24:227-235, 2000.
Scherf, U., et al., "A Gene Expression Database for the Molecular Pharmacology of Cancer," Nature Genetics 24:236-244, 2000.
Walt, D.R., "Molecular Biology: Bead-Based Fiber-Optic Arrays," Science 287(5452):451-452, 2000.
Zhang, L., et al., "Gene Expression Profiles in Normal and Cancer Cells," Science 276:1268-1272, 1997.

* cited by examiner

*Primary Examiner*—Lori A. Clow
(74) *Attorney, Agent, or Firm*—Christensen O'Connor Johnson Kindness PLLC

(57) ABSTRACT

The present invention describes the use of molecular expression profiles in the primary screening of compounds for pharmacological activity. In some embodiments, the methods of the invention comprise characterizing a profile of expression levels of a number of distinct biological molecules for two distinct sample types (A and B) that differ by some relevant parameter, in order to characterize the difference between the two types in terms of expression profile. Following this, one of the types (B) is treated with an analyte of unknown activity relative to the parameter by which the sample types differ. The expression profile of treated B is then measured and compared with the expression profiles of A and untreated B to ascertain whether the analyte has induced a shift in the profile of B to more closely or more distantly resemble the profile of A in some meaningful way.

36 Claims, No Drawings

METHOD FOR SCREENING AND IDENTIFYING PHARMACEUTICAL AGENTS

CROSS-REFERENCE TO RELATED APPLICATION

This application claims priority to now abandoned U.S. patent application No. 60/254,028 filed Dec. 6, 2000.

FIELD OF THE INVENTION

The present invention relates to a method for screening and identifying pharmaceutical agents using molecular expression profiles.

BACKGROUND OF THE INVENTION

Expression pharmacogenomics uses comprehensive differential gene or protein expression profiling to describe drug response in selected model systems, usually with the goal of understanding how drugs exert both therapeutic and toxic effects. Two fundamental principles of expression pharmacogenomics underlie the present invention. The first principle is that each tissue can be characterized by the subset of genes expressed in its cells. This principle holds true for disease states, which can be characterized by disease-specific gene expression profiles. For example, colon cancer cells express a set of genes distinct from those expressed in normal colon cells or other cell types. The differences between the expression profile of disease and normal tissue can be considered a measure of the pathology of the diseased tissue. The second principle is that toxic and therapeutic responses to drugs can be characterized at the molecular level by the set of genes that are perturbed, or differentially regulated, from the normal baseline level of expression. Drugs with therapeutic action on diseased tissue can induce a stereotyped change in the disease's diagnostic gene expression profile. The types of genes that are affected can give insight into the mechanism of the drug, and the induced pattern of expression can serve as a "fingerprint" of the drug's action. Thus, expression pharmacogenomics yields gene expression patterns that are a surrogate measure of tissue physiology or of a compound's therapeutic toxic or biological effect.

A useful technique for the initial identification of drug candidates is high throughput screening of large collections of chemicals, often referred to as "libraries". Most high-throughput screens measure the action of compounds on a single molecular phenomenon, e.g., a particular enzymatic activity that is thought to play a role in some physiological system such as a disease state. Prior to the screening process, the components of such libraries have not been demonstrated to have action on the molecular phenomenon measured by the screen or the disease state in which the molecular phenomena plays a role. Such a screen is designed to identify compounds that affect that particular molecular phenomenon, so that the physiological system in which the phenomena plays a role may be impinged upon with the identified compounds. Previously uncharacterized chemicals that exhibit a specific biochemical activity revealed by the screen are reclassified as "candidate drugs", also known as "hits", "drug candidates" and "drug leads". Such newly-identified candidate drugs subsequently proceed through the drug development pipeline which includes the process of "triage", where candidate drugs are subjected to further characterization and analysis to rank the candidates in order of likely efficacy and toxicity.

This approach has a number of inherent deficiencies. For example, a molecular phenomenon that is a crucial mediator of the physiological system of interest must first be known in order to design a specific screen for agents that affect that phenomenon. Much difficult laboratory research is often required to identify the mechanistic underpinnings of a physiological system of interest. Moreover, the mechanistic molecular phenomenon must lend itself to detection by a screen. Often, devising a detection strategy that is a direct indicator of the molecular phenomenon is impractical with existing technologies available to high throughput screening applications. Another limitation is that compounds that affect the physiological system of interest by some other mechanism than the molecular phenomenon at the heart of the screen are missed, due to the inherent specificity of the screen. Also, compounds identified by the screen may have unknown, undesirable side effects, due to undetected actions on other biological molecular phenomena (i.e., the compound acts nonspecifically on other molecular phenomenon not measured by the screen). Consequently, the overall physiological system can be modified in undesirable and unforeseen ways by compounds identified in the screen. These side effects must be subsequently detected and triaged through costly and inconvenient additional characterization. Another disadvantage lies in that the molecular phenomenon being measured may not be the ideal mediator of the physiological system sought to be influenced (i.e., the target of the screen may not really be a good target). Since the molecular phenomenon at the heart of the screen is only one part of a complex system of which all the component molecular phenomena are usually not known, even a compound that perfectly specifically targets the metric of the screen may not result in the desired final effect on the relevant physiological state.

Gene microarrays are efficient for high throughput triaging of many drug treated samples against a pre-defined set of interesting genes. Expression pharmacogenomics has been used to identify toxicity of previously derived drug leads (Rothberg et al. 2000).

Drug leads have never been derived from a high-throughput screen that uses the gene expression profile as the primary criteria for initial identification of a drug candidate.

SUMMARY OF THE INVENTION

The present invention provides methods that use one or more molecular expression profiles as the parameter measured in primary screens of compounds for pharmacological activity. In one embodiment, the present invention provides a method for identifying compounds with a desired expression profile-altering activity. In the first step, the expression profiles of representative molecules in sample A, for example normal colon tissue, is determined. In the second step, the expression profile of the same molecules is determined for untreated sample B, which differs from sample A in some significant way, for example, colon cancer tissue. In the third step, the expression profile of the same molecules is determined for sample B treated with an analyte or analytes. In the final step, the differences between the expression profiles of sample A and untreated sample B are compared with the differences between the expression profiles of untreated sample B and treated sample B, to identify analytes that induce an expression profile in treated sample B that bears enhanced similarity to the expression profile of sample A. This process can be repeated many times with different analytes, thus constituting a high throughput screen.

Using molecular expression profiles as the measure in primary screening overcomes the shortcomings of screens that seek to identify compounds that affect a particular molecular phenomenon. First, the mechanistic molecular underpinnings of the physiological system of interest need not be known prior to screening. Compounds that act on any effective underlying molecular process, regardless of it's identity or any awareness of mechanism per se, are detected by virtue of their effect on the expression profile. This negates the absolute requirement for detailed initial understanding of the physiology prior to conducting a screen.

Second, effective compounds that act by mechanisms that would be impractical to detect by more focused screens are likely to be detectable by screens that use expression profiling as the measure, because the downstream effect of all compounds that affect the cellular physiology in question is a change in molecular expression profile.

Third, effective compounds working by any number of distinct mechanisms can be identified. Again, because the overall expression profile is the signature of the physiological state of the tissue or cell type, any compound that induces a shift toward the target physiological state is detected, a priori. This presents the corollary benefit that a single screening methodology, rather than multiple independently devised molecularly targeted screens, can be used to detect compounds acting through a variety of different mechanisms.

Fourth, in as much as undesirable effects are discernable by characteristic expression profiles, compounds that negatively affect the expression profile can be initially excluded, regardless of mechanism. Similarly, compounds that elicit untargeted, spurious expression profiles can be excluded, irrespective of whether the untargeted profile elicited is known specifically to correlate with an undesirable physiological process. Ineffective compounds working by any of many distinct mechanisms can thus be identified in the initial screen, thus integrating drug lead identification and triage in a single step, streamlining subsequent characterization and drug development.

Fifth, because the method does not require the identification of a particular biochemical phenomenon as the appropriate target of the compounds being screened, but instead evaluates a downstream diagnostic feature of the overall action, misidentification of molecular targets is not an issue. Compounds that act on targets to ineffectively mediate the physiological state of interest represented by a characteristic molecular expression profile are identified and eliminated at the outset, a priori, even if they act on specific targets that might otherwise be rationally thought to be promising candidate targets, and thus be made the targets of focused high throughput screens.

DETAILED DESCRIPTION OF THE PREFERRED EMBODIMENT

The present invention provides methods that use one or more molecular expression profiles as the parameter measured in primary screens of compounds for pharmacological activity. In one embodiment, the present invention provides a method for identifying compounds with a desired expression profile-altering activity. Stepwise, a procedure employing this strategy could be conducted as described below.

(a) A molecular expression profile is determined for a biological sample of a particular type ("type 1").

(b) An expression profile of the same molecules examined in step (a) is determined for a biological sample of a particular type ("type 2") that is different in some significant way from the sample in step (a).

(c) An expression profile of the same molecules examined in step (a) and (b) is determined for a third biological sample, of type 2, that has additionally been treated with an analyte or analytes with previously experimentally uncharacterized specific pharmacological activity.

(d) Differences between the expression profiles derived in steps (a) and (b) are identified by comparison of the two profiles, to derive "difference profile A". The difference between the two expression profiles derived in steps (b) and (c) is similarly derived ("difference profile B"). Difference profiles A and B are compared to identify whether an analyte has meaningfully influenced some or all of the components of difference profile A (i.e., caused the expression profile of sample type 2 to more favorably resemble the expression profile of sample type 1).

The following definitions are provided in order to provide clarity with respect to the terms as they are used in the specification and claims to describe the present invention.

As used herein, the term "biological sample" refers to any composition of living biological matter. Representative biological samples for use in the method of the invention may derive from a specific cell type in vitro or in vivo; a combination of cell types in vitro or in vivo; a specific tissue type in vitro or in vivo; a combination of tissue types in vitro or in vivo; organs in vitro or in vivo; or an entire single-celled or multi-celled organism.

Biological tissue or cell samples are characterized by the expression of a distinctive set of molecules, conferring an identifying molecular expression profile, or "fingerprint", to the physiological state of the sample. Thus, the term "expression profile" refers to the pattern of expression of a distinctive set of molecules within the biological sample. Representative molecule types that can be characterized for expression profile may include mRNA transcripts or cDNA derived therefrom; proteins; phosphoproteins; carbohydrates; lipids; or any combination or permutation of mRNA transcripts, proteins, phosphoproteins, carbohydrates, and lipids.

Characterization of the profiles of the molecule types described above may be obtained by one or more of the following methods: application of appropriately prepared samples to polynucleic acid microarays, such as has been described by Affymetrix, Inc. or numerous other manufacturers of microarrays, followed by mRNA expression pattern detection; 2-dimensional gel electrophoresis of appropriately prepared samples to derive a pattern of protein expression; application of samples to arrays of antibodies to derive a profile of protein expression; application of samples to arrays of polynucleotides that differentially bind to specific peptides, to derive a pattern of protein expression; analysis of appropriately prepared samples by mass spectrometry to derive mRNA or protein expression pattern; Analysis of appropriately prepared samples by means of application to bead-based mRNA and protein expression analytic methods, such as that described by Lynx Therapeutics, Inc., Illumina, Inc., or Luminex, Inc., to derive mRNA or protein expression pattern; any method other than the above that characterizes a distinctive profile of expression of multiple molecular components of samples.

As used herein, an "analyte" refers to a compound that is being tested for its impact on a particular expression profile when exposed to a biological sample. The analytes of the invention can be obtained using any of the numerous approaches in combinatorial library methods known in the art, including: biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, non-peptide oligomer, or small molecule libraries of compounds (Lam, K. S. (1997) *Anticancer Drug Des.* 12, 145).

Examples of methods for the synthesis of molecular libraries can be found in the art, for example in: DeWitt et al. (1993) *Proc. Natl. Acad. Sci. U.S.A.* 90, 6909; Erb et al. (1994) *Proc. Natl. Acad. Sci. U.S.A.* 91, 11422; Zuckermann et al. (1994) *J. Med. Chem.* 37, 2678; Cho et al. (1993) *Science* 261, 1303; Carrell et al. (1994) *Angew. Chem. Int. Ed. Engl.* 33, 2061; and Gallop et al. (1994) *J. Med. Chem.* 37, 1233.

Libraries of compounds may be presented in solution (e.g. Houghten (1992) *Biotechniques* 13, 412-421), or on beads (Lam (1991) *Nature* 354, 82-84), chips (Fodor (1993) *Nature* 364, 555-556), bacteria or spores (Ladner, U.S. Pat. No. 5,223,409), plasmids (Cull et al. (1992) *Proc. Natl. Acad. Sci. U.S.A.* 89, 1865-1869), or on phage (Scott & Smith (1990) *Science* 249, 386-390; Devlin (1990) *Science* 249, 404-406; Cwirla et al. (1990) *Proc. Natl. Acad. Sci. U.S.A.* 87, 6378-6382; Felici (1991) *J. Mol. Biol.* 222, 301-310).

Libraries, or assemblages, of compounds may also be derived by means other than combinatorial chemistry. The analytes of the invention can be obtained using any of the numerous approaches in library methods known in the art that do not require combinatorial chemistry, such as derivation from natural biological sources, or from non-combinatorial organic synthetic chemistry.

An analyte is defined to have an "expression profile-altering activity" if it elicits a change in the expression profile observed in a biological sample.

As used herein, the term "difference profile" refers to the difference in two or more expression profiles. For example, a difference profile may be derived by comparing the expression profile of two biological samples of different origins, or by comparing the expression profile of a single biological sample before and after treatment with an analyte.

Specific normal states, pathological states, and the effect of pharmaceuticals on pathological or normal states of samples are characterized by molecular mRNA or protein expression profiles detected by such technologies as DNA or antibody microarrays. These molecular expression profiles can be defined as medically desirable or undesirable. The present invention provides a method for deriving such molecular expression profiles when followed by characterization of and comparison with the molecular expression profiles of similar samples treated with analytes that are unknown to have an effect on the specific state represented by the molecular expression profile, in order to evaluate whether those analytes exert a desirable or other specific effect on molecular expression profiles with respect to the expression profiles of relevant tissue. In this way, specific analytes can be evaluated for their action on molecular expression profiles of particular tissues. Analytes found to elicit desirable molecular expression profiles are thus identified as candidate pharmaceutical agents. This method of identification of candidate pharmaceutical agents for the treatment of pathologies lends itself to high-throughput screening of many different compounds for specific action on molecular expression profiles.

Conceptually, this approach may be reduced to three stages: (1) determining an expression profile; (2) deciding on desired changes to the expression profile; (3) detecting an analyte, previously experimentally uncharacterized for specific pharmacological activity, that evokes the desired changes.

The following example is illustrative of a representative method of the invention. For example, in the first stage of the approach the expression levels of 10,000 different mRNA transcripts for a type of prostate cancer cell is determined using DNA microarray technology, a technology with established principles. In short, mRNA of a sample is extracted, enzymatically amplified and labeled with a visualizable moiety, to provide a labeled polynucleic acid. The labeled polynucleic acid is exposed to a microarray upon which have been discretely spotted DNA sequences complimentary to many or all of the possible mRNA species expressed by the sample type. The labeled polynucleic acid species that are expressed by the sample hybridize differentially to the discrete spots, conferring a signal proportional to the concentration of each species in the sample. The intensity of the signal of each of the spots is detected and quantified rapidly using established technology such as a microarray reader. In the second stage, the expression levels of those same mRNA transcripts for normal prostate tissue is determined. The two profiles (prostate cancer, normal prostate) are compared to identify mRNA transcripts with different expression levels between the two tissue types. In the third stage, the cancer cells are treated with a compound of unknown activity on prostate cancer, followed by determination of the mRNA expression levels for the treated cells. This is followed by a determination whether any of the transcripts differentially expressed by the treated cells assume levels characteristic of normal prostate tissue. The final stage of this process is repeated many times with different compounds of unknown activity. This can be done in a high-throughput fashion. In short, for this example, thousands of separate cultures of cancer cells are established in 96-well culture plates. Each well is treated with a different member of a combinatorial chemical library, followed by sample preparation to label the mRNA as described above. Each sample is then exposed to a separate microarray. Each of the microarrays is read by a microarray reader or multiple microarray readers to derive the effect of each chemical library member on the cancer cell expression profile.

Various statistical methods can be used to identify and classify compounds that induce a shift in the cancer expression profile toward the normal tissue expression profile as "hits" (candidate prostate cancer therapeutics). These hits are subjected to further analysis and development as drugs. One method for deriving classifications for expression profiles is with the use of neural network computing (parallel distributed processing, or connectionist processing). For example, a computer neural network is trained to classify general patterns of gene expression. This is accomplished by using the numerical expression level of each component of the profile being measured for a given condition as the input value to a specific processing unit in the input layer of a neural network. The network then uses back propagation to match many example expression profiles to a specific output that represents the appropriate classification of the profile. The same network is trained with examples of expression profiles representing distinct physiological states, where each gene expression level is input to the same processing unit. Thus, a computer neural network learns by example to distinguish between expression profiles representing specific physiological states. A novel expression profile (previously unseen by the network) is then presented as input to the same trained network, which yields output classifying the novel expression pattern in terms of similarity to the patterns it has been trained to recognize. In the example here, a standard three-layer neural network can be used, where each input unit of the neural network corresponds to an individual sequence measured by the array. Thus, the network has 10,000 input units. The network also contains 500 units in the hidden layer and two output units, designated "cancer" and "normal." After sufficient training using a standard back-propagation algorithm, the network correctly classifies the expression patterns of SW837 cells and normal prostate tissue to these respective categories. The weights between processing units are then fixed and the expression values of all 10,000 sequences of the expression profile of each treated sample of SW837 cells from the screen are presented to the input layer. The numerical value of the output units "cancer and "normal" serve to distinguish non-hits from hits, respectively, in the screen.

Using a neural network to conduct the pattern characterization and matching is especially useful when there is variation in the expression profile between samples for a given condition. For example, variations in normal tissue expression profiles between individuals can create background noise that disturbs the detection of "real" signals characterizing normal tissue. Similarly, variations in diseased tissue can obscure disease-related changes in gene expression. Training a neural network with many examples of a given category of profile enables the network to learn the salient and irrelevant features of the profile that it then can use to more effectively categorize novel profiles. One skilled in the art will appreciate that numerous other statistical methods can be utilized in order to categorize the profiles of samples from the screen as "cancer" or "normal."

An additional feature that is useful in expression profiling is the simultaneous detection of the rates of transcription of many genes (L. Peltonen & V. A. McKusick (2001) Science 291: 1224-29). The rates are obtained by rapid sequential array measurements of tissue undergoing some perturbation, such as drug treatment. The array of rates, and rates of change of the rates of expression levels can be considered independently or in combination with absolute expression levels to obtain a more informative expression profile. Thus, one skilled in the art could apply simultaneous detection of the rates of expression of many biological molecules, such as mRNA transcripts, to the method of the present invention.

Another method for deriving expression profiles is SAGE (serial analysis of gene expression). This technique has been used to characterize cancerous colon see the World Wide Web at (ncbi.nlm.gov/SAGE/sagexp.cgi?grpB=166&grpB=167&grpA=171&grpA=172&FACT=2.0&CUTOFFA=0&CUTOFFB=0&nameA=Colon+caner&nameB=Normal+colon) compared with cancerous tissue profiles to identify the 100 genes of those assayed most likely to be expressed differently by at least two-fold between the two tissue types. The same experiment was used in a comparison between brain tumor tissue and normal brain tissue. Thus, one skilled in the art could apply SAGE to the method of the present invention.

The present invention can be used to identify compounds with similar activity to that of known drugs. For example, in the first stage the expression levels of 10,000 different mRNA transcripts for a type of cancer cell is determined using DNA microarray technology. In the second stage, the expression levels of those same mRNA transcripts for the cancer cells treated with a drug known to effectively inhibit that cancer type is determined. The two profiles are compared to identify mRNA transcripts with different expression levels between the two conditions. In the third stage, the cancer cells are treated with compounds of unknown activity followed by a determination of the mRNA expression levels for the treated cells. Finally, the expression profiles are analyzed to determine whether any of the transcripts differentially expressed by the treated cells assume levels characteristic of the cells treated with the known drug. Compounds that induce a shift in the cancer expression profile toward the expression profile of drug treated cells are candidate therapeutics.

Protein microarrays have also been used, in an analogous fashion to DNA microarrays, to profile expression levels of a range of proteins in a sample (A. Leuking et al., (1999) Anal. Biochem. 270:103-11). Thus, one skilled in the art could use protein expression profiling as the metric for screening compounds for biological activity.

A principle advantage of the present invention is that, by comparing the distinctive molecular expression profile of normal, diseased, drug-treated, or genetically manipulated sample tissues or cells with the distinctive molecular expression profile of tissues or cells that have been treated with a novel analyte, the effect of that analyte on expression patterns of pathological, beneficial or otherwise relevant conditions can be evaluated. This approach is especially useful in identifying the potential utility of compounds in disease treatment, when the disease can be characterized at the molecular level by a profile of molecule expression, and an analyte is determined to have a relevant effect on the molecular profile of the disease. Toxicological action of novel analytes may also be discerned by this method, as has been described for methods that use expression profiling to characterize and triage existing drug candidates (Rothberg et al., 2000).

Presently, high-throughput screens of compounds for pharmaceutical action usually evaluate the effect of the compounds on only one enzyme, biochemical process, or marker molecule that is thought to be involved in a disease. However, disease states are characterized by altered cellular processes that bring about numerous changes in the complex molecular regulatory network associated with the disease. Thus, screens evaluating the effect of compounds on a single element can overlook agents that do not directly influence the element being assayed, but do have an overall effect on the disease through another mechanism. By characterizing pathologies in terms of the molecular expression profile, which is affected by the changes in the molecular regulatory network associated with the disease, a comprehensive signature of the disease state can be derived. By designing the screen to include the tens to thousands of molecules that may comprise a molecular expression profile, a broad net is cast to detect agents that desirably alter that profile, and therefore possibly the disease, via any effective mechanism. This approach can also be applied to discovering agents that impinge on cellular states other than pathological ones.

One of the strategies in biomedical research today is to elucidate the underlying genetic architecture involved in complex traits, so that pharmaceuticals may be generated that specifically impinge on the relevant components of that architecture. This goal has been pursued with the use of microarrays and other techniques of molecular expression analysis in order to identify specific genes and pathways underlying diseases and drug response. These genes and pathways then become the focus of functional study and the targets for pharmaceutical development. The approach of the present invention differs from that strategy in practice and philosophy. The present invention utilizes the molecular expression profile as a quantifiable symptom of a pathology, rather than as a means of understanding the underlying root cause so that the root cause may be addressed in a directed fashion with the creation of drugs targeted to specific disease mechanisms. Because the molecular expression profile is likely to be tightly functionally linked to the pathology, agents that are found to influence a pathological expression profile are candidate pharmaceuticals for the treatment of the pathology, irrespective of their specific molecular action. Thus, an advantage of the method of the invention is that no initial understanding of the molecular mechanism of the pathology of the disease or understanding of the molecular action of the agent is required for the initial identification of candidate pharmaceuticals. Any agent found to affect the symptomatic molecular expression profile of a pathology, regardless of the mechanism by which it exerts that effect, is identified as possessing potentially relevant pharmaceutical function.

Another difference between the method of this invention and past practices is that the method of the invention encompasses the screening of compounds with no previously known pharmacological action, in order to identify drug candidates by virtue of molecular expression profile. Also, the method encompasses the screening of compounds with a specific known drug action, in order to identify different, novel drug action of potential pharmacological utility in other pathologies. The method of the invention does not include the screening of compounds with previous biochemically-derived evidence of specific utility (i.e. established drug candidates), in order to identify toxicological molecular expression profiles (see, e.g., Rothberg et al., 2000). Nor does the method of the invention include the screening of established drug candidates, in order to more fully characterize the utility for which they have already been indicated.

The use of the method of the invention to screen components of a combinatorial chemical library, or other assemblage of analytes, for expression profile-inducing activity resembling the expression profile-inducing activity of a known drug differs from the reported comparisons of mRNA transcript expression profiles of cells treated with specific drugs, which seek to analyze the signaling and regulatory pathways affected by the drugs so as to identify the cell-associated drug targets (see, e.g., Gray et al., 1998; Hughes T. R., et al., 2000; Marton M. J. et al., 1998). For example, the report of Gray et al. 1998, compares the mRNA expression profiles elicited by different drugs of previously characterized in vitro activity. The goal and strategy of Gray et al. 1998, was to identify and characterize the molecular pathway targets of specific known enzyme inhibitors, so as to understand their previously identified activity on cells. In contrast, the method of the invention identifies the previously unknown cellular activity and potential pharmacological value of novel analytes based on their action on molecular expression profiles. This contrasts with previous reports analyzing the action of previously identified drugs or drug candidates on expression profiles. The method of the invention facilitates the initial identification of drug candidates, with previously unidentified specific activity, by means of their activity on molecular expression profiles.

The following examples are provided for illustrating, not limiting, the method of the present invention.

EXAMPLES

Example 1

Deriving mRNA Expression Profiles for the Colorectal Cancer SW837 Cell Line and Normal Human Colorectal Cells Using standard sterile cell culture techniques, a 10 cm tissue culture dish is plated with cells of the colorectal cancer SW837 cell line. The cells are grown in Dubecco's Modified Eagle Medium (DMEM), with appropriate nutritional supplements, to 70% confluence. The cells are triturated off plate, pelleted by centrifugation and stored at −80° C.

Normal human colorectal cells isolated from sections of colon mucosa with the use of EDT as described (Nakamura et al. 1993) are cultured in a separate plate. The cells are pelleted and stored at −80° C.

PolyA++ mRNA are isolated for microarray probe synthesis for each sample, as described:

see the World Wide Web at (ra.rprc.washington.edu/microarray/Protocols/QiagenRNAprep.info.010108ks.htm)

2 ug mRNA from each sample are used at a concentration of 1 ug/ul for probe synthesis, followed by hybridization to two separate slide microarrays, as described:

see the World Wide Web at (ra.rprc.washington.edu/microarray/Protocols/ProbeSynandHyb_010209ks.html)

The microarray used is a commercially available cDNA array of 15,000 unique human gene sequences:

see the World Wide Web at (ra.rprc.washington.edu/microarray/Genelists/Human/Human.htm)

Experiments are performed in replicate, and statistical analyses are used as required to sort good data from bad, resulting in the acquisition of a specific gene expression profile for each of the two tissue types being characterized.

Example 2

Using a High Throughput System of Gene Expression Profiling to Derive Individual Expression Profiles for Multiple SW837 Cell Samples, Each Treated with a Different Compound of Unknown Activity on Colorectal Cancer.

SW837 cells are plated into 10 96-well tissue culture plates at 70% confluence (960 wells, total) with the use of a repeat pipetting device. Using a CCS Packard, Inc. MultiPROBE II robotic liquid handling system, 960 components of a pre-existing combinatorial chemical library, in this case originating from Molecumetics, Inc., are prepared for delivery to 96-well tissue culture plates. Using a CCS Packard, Inc. PlateTrak PTS 1014, a different member of the library, at a final concentration of 10 micromolar, is administered to a single well of the tissue culture plates containing the SW837 cells. The culture plates are incubated for 6 hrs at 37° C. Polyadenylated mRNA is extracted from each sample using a Promega MagnaBot 96 magnetic separation device in conjunction with PolyATract mRNA isolation reagents implemented on a Biomek 2000 workstation, as described:

see the World Wide Web at (promega.com/pnotes/75/8554_10/8554_10.pdf)

Using the PlateTrak PTS 1014 to automate liquid handling steps, probes are synthesized in parallel for all samples of each plate. The probes are quantified using a Molecular Devices, Inc. SPECTRAmax PLUS[384], and stored at 20° C. Using a bank of 23 automated slide processors (42 slide capacity/processor)

see the World Wide Web at (ra.rprc.washington.edu/microarray/Presentations/Facilities/sldOO7.htm)

each sample probe is hybridized to a slide microarray of the same sequences used to characterize the expression profiles of normal and untreated SW837 cells (960 microarrays total). Using a Molecular Dynamics GenIII scanning confocal microscope scanner (12 slide capacity)

see the World Wide Web at (ra.rprc.washington.edu/microarray/Presentations/Facilities/sldOO7.htm)

each slide is scanned and expression signals for every sequence of each microarray are recorded using the "spot-on" suite of computerized image and statistical analysis.

Example 3

Identifying Compounds with Desirable Expression Profile-Altering Activity

The expression data from each slide is compared with the expression profiles of the normal and cancer colon cells. Compounds that induce a shift in the expression profile of SW 837 cells toward the expression profile of normal colon tissue are classified as hits and are potentially therapeutic for the treatment of colon cancer. Various statistical techniques may be used in order to classify the expression profile of each treated sample as more closely resembling normal or cancerous cells.

According to one method, the meaningful differences between the respective profiles of normal colon tissue and SW837 cells are first established. As an arbitrary criterion, genes that are expressed at least two-fold more or two-fold less in SW837 cells compared to normal colon tissue are selected as the relevant components of the SW837 cancer cell expression profile. Other criteria may be used. A less stringent criteria would be to identify all genes that differ by a statistically significant amount between the two tissue types, i.e., the ratio must be outside the norm by more than the error in the experiment. The assemblage of genes defined as differentially expressed between the two tissue types is, in this example, the set upon which the action of each compound screened is to be evaluated.

After establishing the identity of the genes differentially expressed between SW837 cells and normal colon tissue, the expression profile of each treated sample from the screen is compared with the identified cohort of differentially expressed genes. Compounds that shift an arbitrary percentage of these differentially expressed genes an arbitrary amount toward the expression levels of normal tissue are classified as hits in the screen. These hits are then further evaluated for effectiveness as pharmaceuticals.

As a measure of the possibly undesirable action of each compound screened, the change induced by the compound on genes that are not differentially expressed between SW837 cells and normal tissue is evaluated. Ideally, a candidate hit does not affect the expression of genes whose expression is stable between the SW837 and normal tissue. Potential hits that induce a certain percentage, such as 5%, of the normally stable genes to change expression level by greater than a certain amount, such as two-fold, are excluded from hit classification. Similarly, potential hits that alter the expression of certain genes, or combinations of genes, in a manner that is known to be contraindicated are excluded from hit classification, as has been described for methods that use expression profiling to characterize and triage existing drug candidates (Rothberg et al., 2000).

The use of a cancer cell line in culture rather than primary cancer tissue presents the complication that some genes that exhibit altered expression in the primary cancer do not exhibit altered expression in the cultured cell line. Moreover, some genes exhibiting altered expression in the cell line do not exhibit altered expression in primary colon cancer tissue, as has been reported (Zhang et al., Gene expression profiles in normal and cancer cells Science vol. 276, 23 May, 1997 p 1268-1272). This can present a problem, because it is possible that the expression profile of the primary cancer is more relevant for the identification of effective compounds than the expression profile of the SW837 cells being treated in the screen. Another classification scheme for hits in this screen is to consider as relevant only the genes whose expression is similarly altered away from normal tissue in both the primary colon cancer and the SW837 colon cancer cell line. The diagnostic expression profile of colon cancer in this scheme is the shared unique components of the expression profiles of the two cancer examples. Compounds that shift an arbitrary percentage of the genes of this diagnostic profile an arbitrary amount toward the expression levels of normal tissue are reclassified from "analyte with uncharacterized action" to "hit" or "candidate drug" or "drug candidate" or "drug lead".

REFERENCES

Each of the following references is incorporated herein by reference in its entirety.

Gray, N. S., Wodicka L, Thunnissen A M, Normal T C, Kwon S, Espinoza F H, Morgan D O, Barnes G, LeClerc S Meijer L, Kim S H, Lockhart D J, Schultz P J. (1998), Exploiting chemical libraries, structure, and genomics in the search for kinase inhibitors, *Science* 281(5376):533-8.

Hughes, T. R. Marton, M J, Jones A R, Roberts C J, Stoughton R, Armour C D, Bennett H A, Coffey E, Dai H, He Y D, Kidd M J, King A M, Meyer M R, Slade D, Lum P Y, Stepaniants S B, Shomaker D D, Gachotte D, Chakraburt K, Simon J, Bard M, Friend S H. (2000), Functional discovery via a compendium of expression profiles, *Cell* 102(1):109-26.

Leuking, A. et al., (1999), *Anal. Biochem.* 270:103-11.

Lockhart, D. J. & Winzeler, E. A. (2000), Genomics, gene expression and DNA arrays. *Nature* 405(6788):827-36.

MacBeath, G. & Schreiber, S. L. (2000), Printing Proteins as Microarrays for High-Throughput Function Determination, *Science* 8; 289(5485): 1760-1763.

Marton M J, DeRisi J L, Bennett H A, Iyer V R, Meyer M R, Roberts C J, Stoughton R, Burchard J, Slade D, Dai H, Bassett D E Jr., Hartwell L H, Brown, P O, Friend S H. (1998) Drug target validation and identification of secondary drug target effects using DNA microarrays. Nature Medicine 4 (11): 1293-301.

Nakamura, S. et al.(1993), *Gut* 34, 1240.

Peltonen, L. & McKusick, V. A. (2001), *Science* 291:1224-29.

Systematic variation in gene expression patterns in human cancer cell lines (2000), *Nat Genet.* 24(3):227-35.

Rothberg, B. E. G., Ramesh T. M., Burgess C. E. (2000), Integrating Expression-based Drug Response and SNP-Based Pharmacogenetic Strategies Into a Single Comprehensive Pharmacoganomics Program, *Drug Development Research* 49:54-64.

Walt, D. R. (2000), Bead-based Fiber-Optic Arrays, *Science* 287: 451-452.

Zhang, et al. (1997), Gene expression profiles in normal and cancer cells, *Science* 276, 1268-1272.

While the preferred embodiment of the invention has been illustrated and described, it will be appreciated that various changes can be made therein without departing from the spirit and scope of the invention.

The invention claimed is:

1. A method for identifying analytes that induce a third expression profile that is more similar to a first expression profile than is a second expression profile, comprising:
   (a) performing an assay to obtain a first expression profile of a set of representative molecules in a first biological sample;
   (b) performing an assay to obtain a second expression profile of the set of molecules in a second biological sample, wherein the second biological sample differs from the first biological sample by a known parameter;
   (c) performing an assay to obtain a third expression profile of the set of molecules in the second biological sample after treatment of the second biological sample with at least one analyte of previously uncharacterized specific pharmacological activity; and
   (d) comparing the third expression profile with the first and second expression profiles to identify one or more analytes that induces a third expression profile that is more similar to the first expression profile than is the second expression profile, wherein the analytes identified as inducing a third expression profile that is more similar to the first expression profile than is a second expression profile is indicative of the identified analytes possessing pharmacological activity.

2. The method of claim 1, wherein step (d) comprises:
   (a) deriving a first difference profile by comparing the first expression profile with the second expression profile;
   (b) deriving a second difference profile by comparing the second expression profile with the third expression profile; and
   (c) comparing the first difference profile with the second difference profile to identify the one or more analytes possessing pharmacological activity.

3. The method of claim 1, wherein identification of the one or more analytes with pharmacological activity comprises classifying the expression profiles obtained in steps (a), (b) and (c) using neural network computing.

4. The method of claim 1, wherein any of the assays are performed using serial analysis of gene expression.

5. The method of claim 1, wherein the first or second biological sample is selected from one or more of the group of a specific cell type in vitro, a combination of cell types in vitro, a specific tissue type in vitro, a combination of tissue types in vitro, organs in vitro, a specific cell type in vivo, a combination of cell types in vivo, a specific tissue type in vivo, a combination of tissue types in vivo, organs in vivo, and an entire single-celled or multicellular organism.

6. The method of claim 1, wherein at least one biological sample is derived from a sample that exhibits a disease condition.

7. The method of claim 1, wherein the representative molecules are selected from the group consisting of mRNA transcripts or cDNA derived therefrom, proteins, phosphoproteins, carbohydrates, and lipids.

8. The method of claim 1, wherein any of the assays are performed using polynucleic acid microarrays.

9. The method of claim 8, wherein the polynucleic acid microarrays comprise elements capable of differentially binding specific peptides.

10. The method of claim 1, wherein performance of at least one of the assays comprises simultaneously detecting the rates of transcriptions of multiple genes.

11. The method of claim 1, wherein any of the assays are performed using capillary electrophoresis.

12. The method of claim 1, wherein any of the assays are performed using 2-dimensional gel electrophoreses.

13. The method of claim 1, wherein any one of the assays are performed using one or more antibodies.

14. The method of claim 1, wherein any of the assays are performed using spectrometry techniques.

15. The method of claim 14, wherein the spectrometry technique is mass spectrometry.

16. The method of claim 1, wherein any of the assays are performed using a method selected from the group consisting of fiber-optic, bead-based mRNA and protein detection.

17. The method of claim 1, wherein any of the assays are performed using differential display.

18. The method of claim 1, wherein step (c) is conducted many times in high-throughput fashion with distinct analytes from a library of analytes.

19. The method of claim 1, wherein the first expression profile of step (a) is derived from a combination of biological samples.

20. The method of claim 1, wherein the tested analyte of step (c) possesses previously characterized pharmacological activity unrelated to the parameter by which the first and second biological samples are known to differ, and where its pharmacological activity relative to said parameter is previously uncharacterized.

21. The method of claim 1, wherein any of the assays are performed using chromatographic techniques.

22. The method of claim 21, wherein the chromatographic technique is HPLC.

23. The method of claim 21, wherein the chromatographic technique is gas chromatography.

24. The method of claim 1, wherein any of the assays are performed using Western blotting.

25. The method of claim 1, wherein the representative molecules are mRNA transcripts.

26. The method of claim 1, wherein the representative molecules are cDNA derived from mRNA transcripts.

27. The method of claim 1, wherein the representative molecules are proteins.

28. The method of claim 1, wherein the representative molecules are phosphoproteins.

29. The method of claim 1, wherein the representative molecules are carbohydrates.

30. The method of claim 1, wherein the representative molecules are lipids.

31. A method for identifying analytes that induce a third expression profile that is more similar to a first expression profile than is a second expression profile, comprising:
   (a) performing an assay to obtain a first expression profile of a set of representative molecules in a first biological sample;
   (b) performing an assay to obtain a second expression profile of the set of molecules in a second biological sample, wherein the second biological sample differs from the first biological sample by exposure to a drug treatment;
   (c) performing an assay to obtain a third expression profile of the set of molecules in a third biological sample after treatment of the third biological sample with at least one analyte of previously uncharacterized specific pharmacological activity with respect to the drug treatment to which the second biological sample was exposed; and
   (d) comparing the third expression profile with the first and second expression profiles to identify one or more analytes that induces a third expression profile that is more similar to the first expression profile than is the second expression profile, wherein the analytes identified as inducing a third expression profile that is more similar to the first expression profile than is the second expression profile is indicative of the identified analytes possessing pharmacological activity with respect to the drug treatment.

32. The method of claim 31, wherein identification of the one or more analytes with pharmacological activity with respect to the drug treatment comprises classifying the expression profiles obtained in steps (a), (b) and (c) using neural network computing.

33. The method of claim 31, wherein any of the assays are performed using serial analysis of gene expression.

34. The method of claim 31, wherein the biological sample is selected from one or more of the group of a specific cell type in vitro, a combination of cell types in vitro, a specific tissue type in vitro, a combination of tissue types in vitro, organs in vitro, a specific cell type in vivo, a combination of cell types in vivo, a specific tissue type in vivo, a combination of tissue types in vivo, organs in vivo, and an entire single-celled or multicellular organism.

35. The method of claim 31, wherein any of the assays are performed using polynucleic acid microarrays.

36. The method of claim 31, wherein step (b) is conducted many times in high-throughput fashion with distinct analytes from a library of analytes.

\* \* \* \* \*

UNITED STATES PATENT AND TRADEMARK OFFICE
CERTIFICATE OF CORRECTION

PATENT NO. : 7,332,272 B1
APPLICATION NO. : 09/935557
DATED : February 19, 2008
INVENTOR(S) : E. Gunther It is certified that error appears in the above-identified patent and that said Letters Patent is hereby corrected as shown below:

ERROR

| | | |
|---|---|---|
| Title Page Item (54) | Title | "METHOD FOR SCREENING AND IDENTIFYING PHARMACEUTICAL AGENTS" should read --METHODS FOR SCREENING AND IDENTIFYING PHARMACEUTICAL AGENTS-- |
| Title Page Item (76) | Inventor | "Bradford," should read --Branford,-- |
| Title Page Item (56) | Refs. Cited (Other Publs., Item 2) | "clincal" should read --clinical-- |
| 1 | 1 | "METHOD FOR SCREENING AND IDENTIFYING PHARMACEUTICAL AGENTS" should read --METHODS FOR SCREENING AND IDENTIFYING PHARMACEUTICAL AGENTS-- |
| 13 (Claim 1, | 21 line 18) | "induces" should read --induce-- |
| 13 (Claim 1, | 26 line 23) | "profile is" should read --profile are-- |
| 13 (Claim 7, | 56-57 lines 3-4) | "phosphop-proteins," should read --phospho-proteins,-- |
| 14 (Claim 31, | 66 line 21) | "induces" should read --induce-- |

UNITED STATES PATENT AND TRADEMARK OFFICE
CERTIFICATE OF CORRECTION

PATENT NO. : 7,332,272 B1
APPLICATION NO. : 09/935557
DATED : February 19, 2008
INVENTOR(S) : E. Gunther It is certified that error appears in the above-identified patent and that said Letters Patent is hereby corrected as shown below:

ERROR

| 15 (Claim 31, | 5 line 26) | "profile is" should read --profile are-- |

Signed and Sealed this

Eighteenth Day of November, 2008

JON W. DUDAS
*Director of the United States Patent and Trademark Office*